(12) United States Patent
Necessary et al.

(10) Patent No.: US 10,636,324 B2
(45) Date of Patent: Apr. 28, 2020

(54) DEVICE FOR TRAINING TRACHEAL SUCTIONING

(71) Applicant: Laerdal Medical AS, Stavanger (NO)

(72) Inventors: Greg Necessary, Gatesville, TX (US); Ben Tedeschi, Lorena, TX (US); Paul Griffith, Gatesville, TX (US); David Thane, McGregor, TX (US)

(73) Assignee: Laerdal Medical AS, Stavanger (NO)

( * ) Notice: Subject to any disclaimer, the term of this patent is extended or adjusted under 35 U.S.C. 154(b) by 230 days.

(21) Appl. No.: 15/851,165

(22) Filed: Dec. 21, 2017

(65) Prior Publication Data

US 2019/0197921 A1  Jun. 27, 2019

(51) Int. Cl.
| | |
|---|---|
| *G09B 23/28* | (2006.01) |
| *A61M 16/04* | (2006.01) |
| *G09B 23/32* | (2006.01) |
| *G09B 23/34* | (2006.01) |
| *G09B 23/30* | (2006.01) |

(52) U.S. Cl.
CPC ....... *G09B 23/288* (2013.01); *A61M 16/0463* (2013.01); *A61M 16/0475* (2014.02); *G09B 23/285* (2013.01); *G09B 23/30* (2013.01); *G09B 23/32* (2013.01); *G09B 23/34* (2013.01)

(58) Field of Classification Search
USPC .......... 434/262, 265, 267, 268, 272
See application file for complete search history.

(56) References Cited

U.S. PATENT DOCUMENTS

| | | | |
|---|---|---|---|
| 5,339,808 A | 8/1994 | Don Michael | |
| 9,721,483 B2* | 8/2017 | Cowperthwait | G09B 23/288 |
| 2007/0218438 A1 | 9/2007 | Sanders et al. | |
| 2009/0192505 A1* | 7/2009 | Askew | A61B 18/0218 606/21 |
| 2014/0090194 A1 | 4/2014 | Stadelman et al. | |
| 2014/0302475 A1 | 10/2014 | Sakezles | |
| 2015/0024361 A1* | 1/2015 | Williams | G09B 23/288 434/265 |
| 2016/0379526 A1* | 12/2016 | Frembgen | G09B 23/285 434/272 |

FOREIGN PATENT DOCUMENTS

| | | |
|---|---|---|
| CN | 205091958 U | 3/2016 |
| FR | 3011474 A1 | 4/2015 |

* cited by examiner

*Primary Examiner* — Kurt Fernstrom
(74) *Attorney, Agent, or Firm* — Winstead PC

(57) ABSTRACT

Training device for training tracheal suctioning. The training device includes a tracheal core adapted to be arranged within a tracheal, nasal or oral cavity of a medical training simulator, and coupled to the airways of the simulator and an insert adapted to be inserted into the core, the insert forming a reservoir for simulated mucus.

9 Claims, 3 Drawing Sheets

DEVICE FOR TRAINING TRACHEAL SUCTIONING

TECHNICAL FIELD

The present invention relates to training equipment for medical training of health workers, such as paramedics or physicians or nurses. It specifically concerns a device for training tracheal suctioning on a medical simulator, such as a manikin.

BACKGROUND ART

A medical simulator, such as a manikin is commonly equipped with oral and nasal airways that are communicating with a simulated lung. The lung is fluidly coupled to the airways through a tube extending from the head portion, through a neck portion, and into a chest portion wherein the lung is arranged. In most manikins, there are two lungs that are each coupled via a simulated bronchus to a common simulated trachea. The bronchi and the trachea are constituted by tubes.

Such manikins are frequently used by medical staff or the populace to train CPR or more advanced medical procedures, depending on the design of the manikin.

The device is primarily intended for insertion through an opening made at the throat of the manikin. The opening connects with the tube forming the trachea of the manikin. This provides valuable training for tracheotomy, where an incision has to be made at the throat of the patient to make a slit through the skin and the trachea of the patient. When the slit has been made, a tracheostomy tube is inserted through the slit and into the trachea. In a manikin, the slit is conveniently already present, but has to be opened by insertion of a tracheostomy tube.

To avoid pollution of the tubes and lungs, and hence the necessity of cleaning and disinfection, during the performance of CPR, means, such as a ventilator cloth, are commonly used. This will largely prevent saliva and germs to enter the airways.

However, such a cloth or other means that are designed to prevent droplets from entering the airways are not possible to use when training on tracheal suctioning where a catheter or thin tube is inserted through the tracheostomy tube to suck out any mucus in the airways.

Consequently, such suction training is often done as "dry training", without any fluids being present. This dry suction may not provide adequate training as the health worker will not know is if sufficient or any mucus would have been sucked out by the procedure. It is therefore desirable to have a simulated mucus present in the airways. The simulated mucus will add realism to the training and the health worker will instantly know from the flow of simulated mucus through the suction device that the suction is being performed correctly.

Removal of mucus from the airways prior to ventilation is important, as the mucus may prevent air from entering the lungs and the mucus may be forced into the lungs by the air ventilation pressure. Mucus in the lungs may cause harm to the patient and prevent air from properly entering the lungs.

CN205091958 describes a simulator for simulating removal of retentate liquid above an airbag by the impact airflow caused by simple respirator-assisted ventilation, when a tracheal tube with an airbag has been inserted into the trachea. Retenate liquid is retained by a filter and collected in a collection container.

This device is for simulating a different procedure than the procedure that the present invention is intended to simulate. This known device cannot be used for simulating tracheal suction.

Consequently, there is a need for a device that will enable simulated tracheal suctioning without the risk of any simulated mucus entering the airways and the lungs of the medical simulator.

SUMMARY

The present invention has as an object to provide a device that enables realistic training on tracheal suction and ventilation through the tracheostomy tube without the risk of simulated mucus entering the lungs of the manikin.

BRIEF DESCRIPTION OF DRAWINGS

The invention will be described referring to the accompanying drawings, in which.

DETAILED DESCRIPTION

Figure 1:
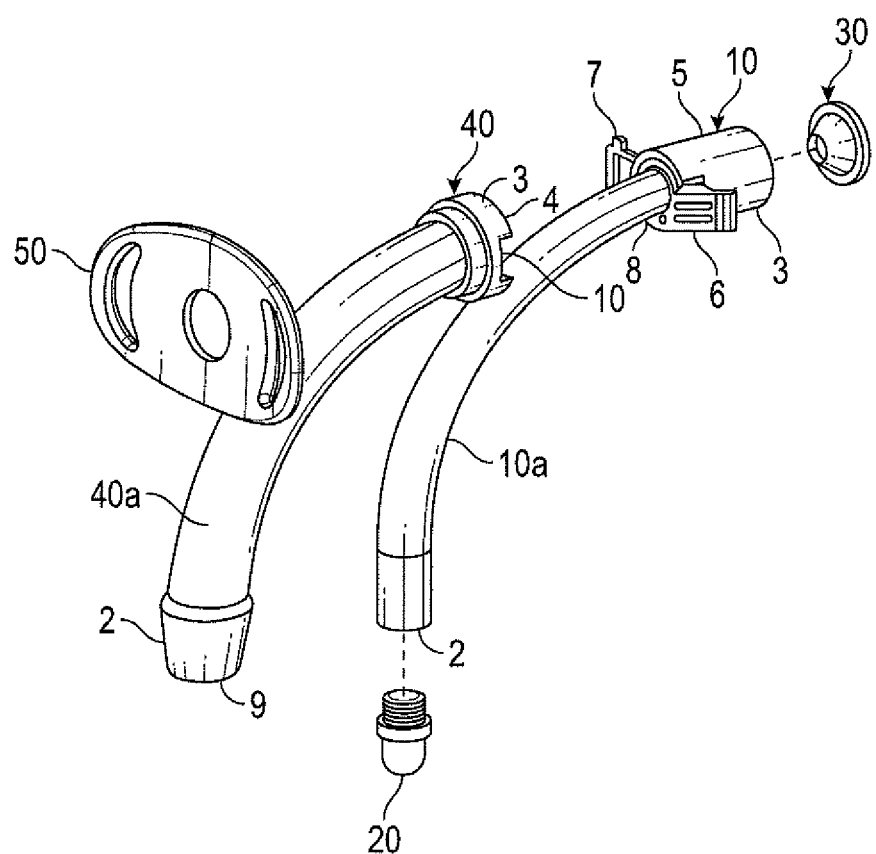
FIG. 1 shows the device of the invention in exploded view.

The training device 1 of the invention is primarily adapted to enter through a trachea opening or slit at the throat of a manikin 60 (FIG. 3), but may also be used through the mouth 62 (FIG. 3) or nose opening 63 (FIG. 3) of a manikin. It has a distal end 2, which is put through the trachea opening 64 (FIG. 3) and a proximal end 3, which is adapted to stay at the outside of the throat close to the trachea opening 64.

As shown in FIG. 1, the device 1 comprises a tracheal core 40, which has a tubular part 40a that at the distal end 2 is adapted to be arranged within the tracheal tube 61 (FIG. 3) of the manikin 60, which in turn is leading to the lower airways, including the lungs. At the proximal end 3, the tracheal core 40 has a flange 4, which will be explained further hereinafter.

The device also comprises a tracheal insert 10, which comprises a tubular part 10a. At the distal end 2 it may be equipped with a plug 20, but in a preferred embodiment, the distal end is closed. If a plug 20 is used, there may be a friction fit between the inside of the insert 10 and the plug 20 to form an airtight fit. Another less preferred option is that the plug 20 may have threads that are received by corresponding threads at the inside of the insert 10 to form an airtight fit.

At the proximal end 3, the insert 10 has a sleeve fitting 5, which is equipped with a pair of tabs 6, 7 that are coupled to the sleeve fitting 5 through a living hinge.

Between the sleeve fitting 5 and the tubular part 10a are a plurality of vent openings 8. These openings may be provided with a filter that prevents the passing of liquid there through.

At the proximal end of the sleeve fitting, opposite of the tubular part, an insert funnel 30 is provided. The insert will hide the vent openings 8. The insert funnel 30 has a conical shape to facilitate the entry of a suction hose (not shown).

A neck flange 50 may be provided around the tracheal core 40 and arranged immediately distal of the flange 4, to secure the device 1 to the manikin 60. The core 40 may be equipped with an inflatable cuff (not shown) on the outside, to make a tight seal between the trachea and the core. The neck flange has slits that are adapted to receive a strap (not shown) that can be secured around the neck of the manikin 60.

Figure 3:
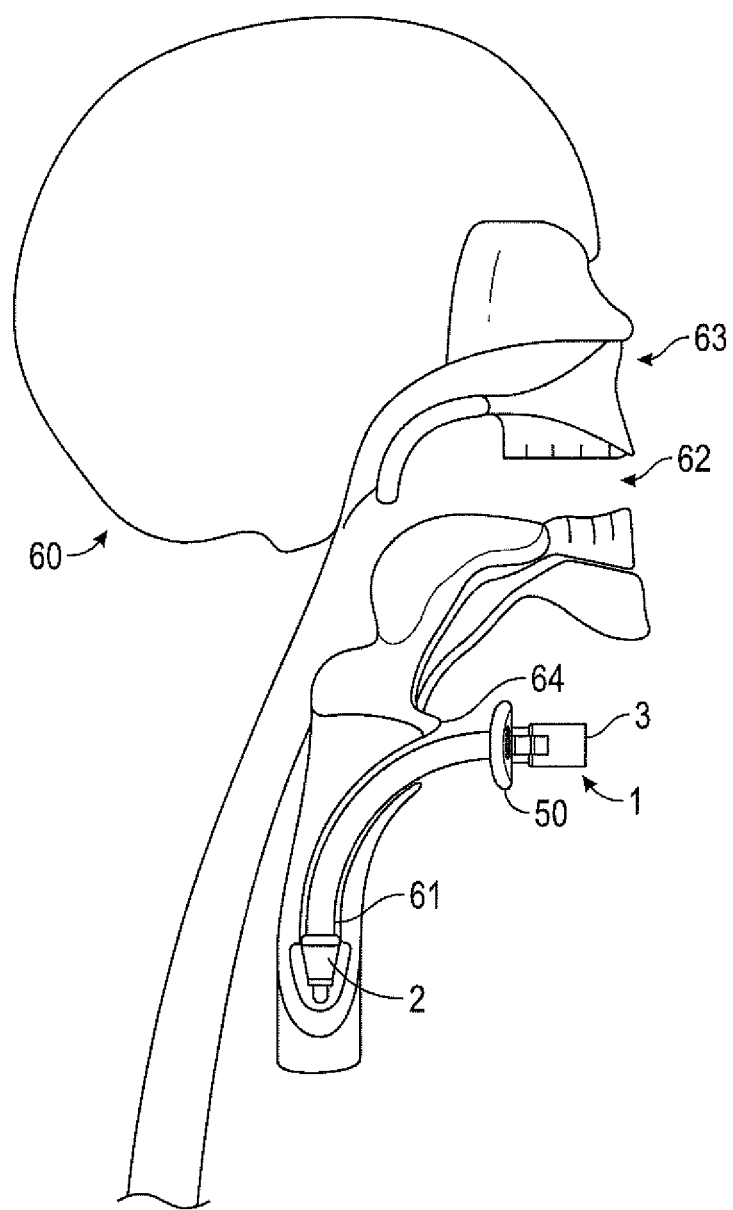
FIG. 3 shows the device of the invention arranged in a manikin.

When used, the core 40 is put into the trachea opening at the throat of the manikin as shown in FIG. 3. The distal end 2 has a conical portion 9, which is adapted to be received with close fit by the airway tube of the manikin.
Straps are lead around the neck of the manikin and secured to the neck flange 50.

Next, the plug 20 (if one is present) is screwed into the distal end 2 of the tracheal insert 10. Then the insert 10 is filled with simulated mucus and fed into the open proximal end 3 of the core 40. The tabs are aligns with notches 10 on the flange 4 and grip behind the flange 4 to secure the insert to the core 40 and create a seal between the insert and the core.

Figure 2:
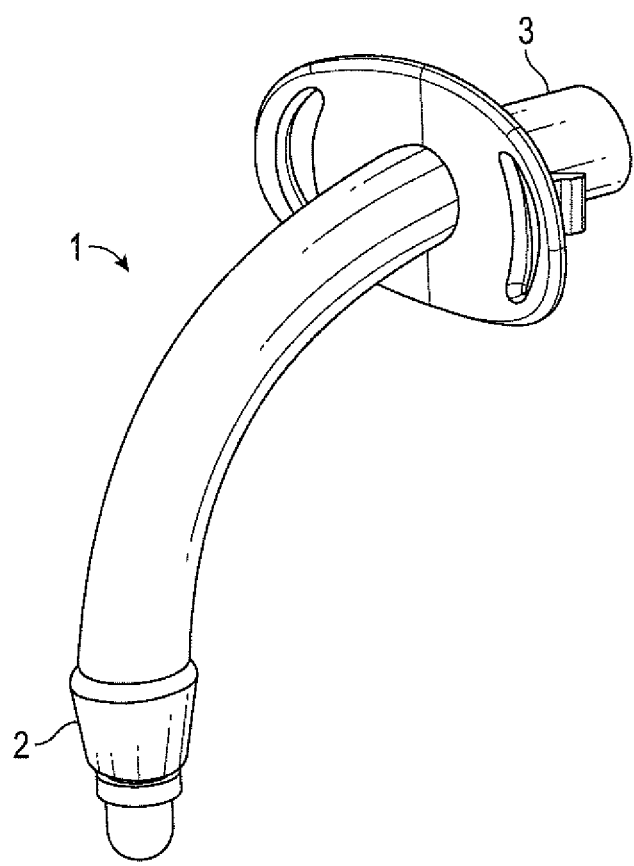
FIG. 2 shows the device of the invention in assemble view.

The insert funnel 30 is preferably permanently affixed to the proximal end of the sleeve 5 during manufacturing. The assembled device will then be as shown in FIG. 2 (the manikin is not shown in this figure).

To train on tracheal suction the student will feed a suction hose (not shown), which at the outer end is coupled to a syringe or similar device, into the opening formed by the insert funnel 30. The hose will be centered within the sleeve 5 due to the funnel 30 and easily enter the insert 10. The hose can be fed all the way to the bottom of the insert 10, which interior is acting a reservoir for the simulated mucus.

The reservoir in the insert 10 will be filled with mucus before training and when the suction hose is in place. The suction training may then commence and the student as well as the teacher can observe and hear the mucus being sucked out.

Ventilation of the manikin 60 can be done unhindered by the training device of the invention. Ventilation air will be forced in through the insert funnel 30. The air cannot enter the interior of the insert 10, as this is closed at the distal end 2, either by this end being closed off or because of the plug 20. The air instead flows through the plurality of openings 8 and onto the core 40. As the core 40 is coupled to the airways of the manikin 60, the air will then flow into the lungs (not shown).

When the lungs have been filled and the ventilation pressure is released, air will flow out the opposite way, from the airways of the manikin into the core 40, through the plurality of openings 8 and out through the funnel 30.

To ensure that no liquid may be drawn into the airways, the plurality of openings 8 may be equipped with the filter material that effectively prevents liquid droplets from passing through.

This way, the airways may be kept clean and dry throughout the procedures.

When the training is done, the insert 10 may easily be removed by gripping the tabs 6, 7 and bring them out of the engagement with the flange 4. Then the insert can be slid out of the core 40. If a plug 20 is present, it can be unscrewed to facilitate cleaning of the insert. If the insert 10 has a permanently closed distal end, the insert may still be cleaned by flushing the interior of the insert.

The core 40 and the neck flange 50 may optionally be left in place until the next training or may be removed by releasing the straps and pulling out the core 40. The insert may also be left in place during multiple subsequent trainings.

The core can be adapted to fit any manikin 60 that comprises a tracheal opening or an oral or a nasal opening and airways.

FIG. 3 shows the manikin 60 the training device 1 inserted into the tracheal opening of the manikin 64.

The invention claimed is:

1. A training device for training tracheal suctioning, the training device comprising:
    a tracheal core adapted to be arranged within a tracheal, nasal or oral cavity of a medical training simulator, and coupled to airways of the medical training simulator; and
    an insert adapted to be inserted into the core, the insert forming a reservoir for simulated mucus.

2. The training device of claim 1, wherein a proximal end of the insert protrudes out of a proximal end of the core when fully arranged in the core, forming an opening for a suction hose.

3. The training device of claim 1, wherein the core and the insert are equipped with interfaces enabling the insert to be secured to the core.

4. The training device of claim 1, wherein air openings are formed between the insert and a proximal end of the core to enable air to enter or escape from the core through a proximal opening of the insert.

5. The training device of claim 4, wherein the air openings are formed at a distal end of a sleeve that has a larger diameter than an insert tube of the insert.

6. The training device of claim 1, wherein a distal end of said insert is a closed end, the closed end being adapted to be arranged within the core.

7. The training device of claim 1, wherein an insert funnel is adapted to be arranged in an opening at a proximal end of the insert.

8. The training device of claim 1, wherein a neck flange is adapted to be fixated to the core, the neck flange being adapted to receive a neck strap, which in turn is adapted to secure the neck flange to the manikin.

9. The training device of claim 1, wherein the insert has an outer diameter that is smaller than an inside diameter of the core to allow air to pass therebetween.

* * * * *